United States Patent [19]
Yoshioka et al.

[11] Patent Number: 5,378,611
[45] Date of Patent: Jan. 3, 1995

[54] PROCESS FOR PRODUCING 6β,14α-DIHYDROXY-4-ANDROSTENE-3, 17-DIONE AMID 14α-HYDROXY-4-ANDROSTENE-3,6,17-TRIONE FROM 4-ANDROSTENE-3, 17-DIONE USING MYROTHECIUM SP. FERM BP-4432

[75] Inventors: Hideki Yoshioka; Hajime Asada, both of Takasaki; Shinji Fujita, Yono, all of Japan

[73] Assignee: Nippon Kayaku Kabushiki Kaisha, Tokyo, Japan

[21] Appl. No.: 154,857

[22] Filed: Nov. 19, 1993

[30] Foreign Application Priority Data

Nov. 27, 1992 [JP] Japan .................. 4-339578
Oct. 6, 1993 [JP] Japan .................. 5-272912

[51] Int. Cl.⁶ .............. C12P 33/06; C12P 33/16; C12P 33/02; C12N 1/14
[52] U.S. Cl. .............. 435/58; 435/61; 435/54; 435/52; 435/254.1; 435/911
[58] Field of Search .............. 435/53, 911, 53, 58, 435/254.1, 52, 61; 436/254.1

[56] References Cited

U.S. PATENT DOCUMENTS

| 4,382,952 | 5/1987 | Bloem et al. | 424/279 |
| 4,999,357 | 3/1991 | Gadras et al. | 514/277 |
| 5,180,827 | 1/1993 | Gadras et al. | 546/19 |
| 5,258,290 | 11/1993 | Weber et al. | 435/119 |
| 5,275,949 | 1/1994 | Sakamoto et al. | 435/280 |

FOREIGN PATENT DOCUMENTS

0300062 1/1989 European Pat. Off.

*Primary Examiner*—Douglas W. Robinson
*Assistant Examiner*—Jeffrey J. Sevigny
*Attorney, Agent, or Firm*—Nields & Lemack

[57] ABSTRACT

The invention provides a novel process for the production of 6β,14α-dihydroxy-4-androstene-3,17-dione which comprises culturing a microorganism belonging to the genus Myrothecium and capable of hydrolyzing 4-androstene-3,17-dione to produce 6β,14α-dihydroxy-4-androstene-3,17-dione in a medium supplemented with 4-androstene-3,17-dione, and isolating 6β,14α-dihydroxy-4-androstene-3,17-dione from the cultured medium. According to the process of the present invention, 6β,14α-dihydroxy-4-androstene-3,17-dione and 14α-hydroxy-4-androstene-3,6,17-trione can be produced with a high yield in a simple manner.

3 Claims, No Drawings

PROCESS FOR PRODUCING 6β,14α-DIHYDROXY-4-ANDROSTENE-3,17-DIONE AMID 14α-HYDROXY-4-ANDROSTENE-3,6,17-TRIONE FROM 4-ANDROSTENE-3,17-DIONE USING MYROTHECIUM SP. FERM BP-4432

BACKGROUND OF THE INVENTION

1. Field of the Invention

The present invention relates to a novel process for the production of 6β,14α-dihydroxy-4-androstene-3,17-dione and 14α-hydroxy-4-androstene-3,6,17-trione which are known androstene derivatives and reported to exhibit an androgen action, an aromatase activity-inhibitory action, or an action of inhibiting cell proliferation against human breast cancer cells.

2. Related Art Statement

As a process for preparing 6β,14α-dihydroxy-4-androstene-3,17-dione shown by formula 1:

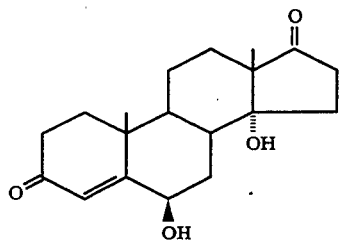

there is known a process which comprises culturing a strain belonging to the genus Acremonium, e.g., *Acremonium strictum*, in a nutrient medium and isolating 6β,14α-dihydroxy-4-androstene-3,17-dione from the fermentation broth [Japanese Patent KOKAI (Laid-Open) No. 63-192796].

However, the known process involves problems that the yield of 6β,14α-dihydroxy-4-androstene-3,17-dione is low and the purified product is not obtained in a sufficient amount because of the presence of by-products produced by the process.

Another known process comprises culturing a specific strain belonging to the genus Acremonium, i.e., *Acremonium strictum* (supra), in a medium containing nutrient sources, isolating 6β,14α-dihydroxy-4-androstene-3,17-dione from the fermentation broth and oxidizing the dione compound to 14α-hydroxy-4-androstene-3,6,17-trione [Japanese Patent KOKOKU (Post-Exam Publn) No. 1-32236]. The trione compound is expected to be useful as a carcinostatic agent. However, this process also encounters a disadvantage that the yield of 14α-hydroxy-4-androstene-3,6,17-trione is low.

SUMMARY OF THE INVENTION

An object of the present invention is to eliminate the foregoing problems and provide a novel process for producing 6β,14α-dihydroxy-4-androstene-3,17-dione and 14α-hydroxy-4-androstene-3,6,17-trione.

For the purpose of developing an efficient process for production of 6β,14α-dihydroxy-4-androstene-3,17-dione, the present inventors have isolated a number of microorganisms from the soil and investigated their production efficiency. It has thus been found that microorganism belonging to the genus Myrothecium can efficiently produce 6β,14α-dihydroxy-4-androstene-3,17-dione with minimized production of the by-products.

A first aspect of the invention is a process which comprises culturing a microorganism belonging to the genus Myrothecium and capable of hydroxylating 4-androstene-3,17-dione to produce 6β,14α-dihydroxy-4-androstene-3,17-dione in a medium supplemented with 4-androstene-3,17-dione, and isolating 6β,14α-dihydroxy-4-androstene-3,17-dione from the fermentation broth.

A second aspect of the invention is a microorganism belonging to the genus Myrothecium and capable of hydroxylating 4-androstene-3,17-dione to produce 6β,14α-dihydroxy-4-androstene-3,17-dione.

A third aspect of the invention is a process for producing 14α-hydroxy-4-androstene-3,6,17-trione which comprises hydroxylating 4-androstene-3,17-dione by the microorganism defined above, oxidizing the resulting 6β,14α-dihydroxy-4-androstene-3,17-dione to 14α-hydroxy-4-androstene-3,6,17-trione; wherein a microorganism is cultured which belongs to the genus Myrothecium and is capable of hydroxylating 4-androstene-3,17-dione to produce 6β,14α-dihydroxy-4-androstene-3,17-dione in a medium supplemented with 4-androstene-3,17-dione, and the resulting 6β,14α-dihydroxy-4-androstene-3,17-dione is isolated from the fermentation broth.

DETAILED DESCRIPTION OF THE INVENTION

The product isolated from the fermentation broth was investigated with respect to its physico-chemical properties. The results reveal that the product coincided with authentic 6β,14α-dihydroxy-4-androstene-3,17-dione.

The physico-chemical properties of the product are shown below.

| | | |
|---|---|---|
| (1) | Appearance | white powder |
| (2) | Molecular weight | 318 |
| (3) | Molecular equation | $C_{19}H_{26}O_4$ |
| (4) | Melting point | 256–257° C. |
| (5) | UV absorption spectra | maximum absorption: 236 nm (neutral, in methanol) |
| (6) | EI mass spectrum | m/z = 318 |
| (7) | IR absorption spectra | (KBr method) 3460, 2960, 1748, 1682, 1650 $cm^{-1}$ |
| (8) | Protonic nuclear magnetic resonance spectra (CDCl$_3$) | δ ppm; 18-H: 1.08 (3H, s) 19-H: 1.42 (3H, s) 6-H: 4.49 (1H, t) 4-H: 5.83 (1H, s) |
| (9) | $^{13}$C-Nuclear magnetic resonance spectra (CDCl$_3$) | δ ppm; C-1: 34.3, C-2: 32.6, C-3: 200.4, C-4: 126.8, C-5: 167.4, C-6: 73.0, C-7: 37.3, C-8: 32.6, C-9: 47.0 C-10: 38.5, C-11: 19.4, C-12: 24.7, C-13: 52.9, C-14: 80.5, C-15: 30.3, C-16: 33.0, C-17: 218.2, C-18: 18.0, C-19: 19.6 |

A specific example of the microorganism which can be used in the present invention is Myrothecium sp. NK-928521. In addition to this strain, all microorganisms, including natural and artificial mutants can be also used in the present invention so long as these microorganisms belong to the genus Myrothecium and are capable of hydroxylating 4-androstene-3,17-dione to produce 6β,14α-dihydroxy-4-androstene-3,17-dione. Artificial mutants can be obtained in a conventional manner such as a treatment by exposure to UV ray.

The strain NK-928521 has the following microbiological properties.

(1) Growth conditions in various media

The growth conditions of the strain NK-928521 in various agar media are shown in the table below.

The conditions were observed after the strain had been cultured at 25° C. for 14 days.

TABLE 1

Growth Conditions in Media

| | | |
|---|---|---|
| (1) | Potato-dextrose-agar medium | It grows extremely well to reach a colony diameter of 63.0 mm. On the colony surfaces fluffy or wooly aerial hyphae grow thick to show a color of white. The rear surfaces have the same color as that of the surfaces. |
| (2) | Malt extract-agar medium | It grows extremely well to reach a colony diameter of 58.3 mm. Woolly aerial hyphae grow on the colony surfaces to show a color of white to yellow ocher. The rear surfaces have the same color as that of the surfaces. |
| (3) | Czapek agar medium | It grows well and a colony diameter reaches 64.5 mm. On the colony surfaces aerial hyphae grow thin. Vegetative hyphae are latent. |
| (4) | Oatmeal-agar medium | It grows well and a colony diameter reaches 63.5 mm. On the colony surfaces woolly aerial hyphae grow belt-like to form a color of white. |
| (5) | Corn meal-agar medium | It grows well and a colony diameter reaches 69.3 mm. On the colony surfaces loose woolly aerial hyphae grow thin. Vegetative hyphae are latent. |

Conidiogenus-cells of this strain gather at the sporodochium of a light olive to black green color with sporadic or white periphery on the corn meal agar medium. Formation of conidia on the medium requires 3 to 4 weeks. The hyphae with septa are colorless, smooth and thin; the septa have a width of 2.0 to 3.0 μm. Conidiophore is formed with a thin colorless acevulus. The peripheral hyphae with septa are twisted, branched, colorless and smooth.

Conidiophore is composed of a thin sporodochium and branched with repetition. Each ramus has further 2 to 4 ramuli and phialides grow on the last ramulus. Conidiophores are colorless and have septa. A size of the cells is 7.0–15.0×2.0–3.0 μm. Two to six phialides are verticillate and attached closely to each other to become stratiform; cylindrical (8.0–16.0×2.0–3.0 μm), colorless. The conidium-bearing periphery becomes a dark color.

Conidia are ship-shaped, spindle-shaped or lemon-shaped (5.0–7.0×2.1–4.0 μm), projected pruncate base and form a color of brownish olive. The surfaces are smooth and most conidia gather as a slime mass on the sporodochium.

(2) Physiological properties

The optimum growth temperature is about 25° C. The microorganism grows at 10°–33° C., preferably at 20°–30° C., but does not grow at 37° C. The optimum growth pH is about 6.0. The microorganism grows at pH of 4.0 to 8.0.

Based on the foregoing microbiological properties, it is clearly shown by Ainsworth, G. C.: Ainsworth and Bisby's Dictionary of the Fungi, 7th ed. (by Hawksworth, Sutton, and Ainsworth), CMI, Kew (1983) that the microorganism is a strain belonging to the genus Myrothecium of the division Eumycota, the subdivision Deuteromycotina, the class Hyphomycetes. The microorganism is thus identified as Myrothecium sp. NK-928521.

The strain NK928521 was deposited with National Institute Bioscience and Human-Technology Agency of Industrial Science and Technology (Ibarakiken, Japan) on Oct. 29, 1992, and received FERM P-13234 as an accession number. Then, the deposition was transferred into an international deposition under the Budapest Treaty on Oct. 1, 1993, and received FERM BP-4432 as an accession number.

The process of the present invention for producing 6β,14α-dihydroxy-4-androstene-3,17-dione is performed by supplementing 4-androstene-3,17-dione as a substrate to an ordinary medium appropriately containing the carbon sources, nitrogen sources, inorganic substances and other trace nutrients required for the strain used, and then culturing the strain in such a medium. As carbon sources, there may be used, in addition to glycerine, for example, glucose, fructose, sucrose, maltose, lactose, dextrin, starch, thick malt syrup, molasses, oils and fats, organic acids, or the like. Among the carbon sources, sucrose is preferred.

Examples of the nitrogen sources include organic or inorganic nitrogen compounds such as soybean meal, cotton seed powders, corn steep liquor (C.S.L.), peptone, casein, Casamino acid, yeast extract, germ, meat extract, urea, amino acids and ammonium salts. Of these nitrogen sources, soybean meal and C.S.L. are preferably used. As inorganic compounds, inorganic salts such as sodium, potassium, calcium and magnesium salts or phosphates are used singly or in an appropriate combination thereof.

The medium may also appropriately contain heavy metals such as iron, copper, zinc, manganese and cobalt salts, or vitamins such as biotin and vitamin $B_1$, if necessary and desired. Surface active agents such as silicone and polyalkylene glycol ethers may also be supplemented in the medium.

For cultivation, a conventional technique used for cultivation of microorganisms is used but liquid culture, especially shaking culture and deep aerated agitation culture are most suited for the cultivation. The culture temperature is generally between 10° C. and 33° C., preferably between 20° C. and 30° C. The pH for cultivation is generally in the range of 2 to 8, preferably 4 to 7.

A period of time required for cultivation varies depending upon culture conditions but is generally 1 to 10 days. A concentration of 4-androstene-3,17-dione in the medium is generally in the range of 0.02 to 2.0% (w/v), preferably 0.1 to 1.5% (w/v).

Timing for adding 4-androstene-3,17-dione to the medium is not particularly limited; the substrate may be present as a component of the medium at the time when cultivation starts, or may also be added continuously or intermittently during the course of cultivation. Where carbon sources such as glucose, maltose and sucrose or nitrogen sources such as peptone and yeast extract are supplemented during the cultivation, the substrate may be added to the medium together with these carbon sources or nitrogen sources.

After completion of the cultivation, 6β,14α-dihydroxy-4-androstene-3,17-dione accumulated in the fermentation broth is harvested from the broth by utilizing the physico-chemical nature of the product.

That is, 6β,14α-dihydroxy-4-androstene-3,17-dione is contained in the cell-containing insoluble fraction and the filtrate of the fermentation broth. Accordingly, the fermentation broth is centrifuged or filtered to be separated into the cell-containing insoluble fraction and the filtrate. Then, the desired 6β,14α-dihydroxy-4-androstene-3,17-dione can be extracted and collected.

The desired product may also be harvested by directly extracting from the fermentation broth with a non-aqueous organic solvent, e.g., chloroform, ethyl acetate, butyl acetate, butanol, methyl isobutyl ketone, or the like.

For isolation of 6β,14α-dihydroxy-4-androstene-3,17-dione from the filtrate of the fermentation broth, the filtrate is adsorbed onto carriers such as activated charcoal, cellulose powders and adsorbent resin (e.g., polystyrene type porous polymer gel, methacrylate type porous polymer gel, spherical porous gel of polyvinyl alcohol, acrylate type porous polymer gel or the like), followed by elution with an appropriate solvent.

From these carriers, 6β,14α-dihydroxy-4-androstene-3,17-dione is eluted with a water-miscible organic solvent such as aqueous alcohol and aqueous acetone. The thus eluted 6β,14α-dihydroxy-4-androstene-3,17-dione may be further purified by column chromatography, if necessary and desired.

From the insoluble fraction containing the culture cells, 6β,14α-dihydroxy-4-androstene-3,17-dione is isolated and recovered by extracting the product from the insoluble fraction with a water-miscible organic solvent such as acetone and ethanol. The extracted product can be further purified by a conventional method used for purification of steroids. Such a method is, for example, column chromatography using a carrier such as silica gel, activated alumina and adsorbent resin.

In column chromatography using silica gel as a carrier, elution is effected by using appropriate solvents, singly or in combination, such as chloroform, ethyl acetate, acetone and methanol. High performance liquid chromatography technique may also be advantageously used for the isolation and purification of the product. Typical examples of the carrier which may be used include silica gel, and chemical binding type silica gel obtained by chemically binding octadecyl, amino or octyl to silica gel, or adsorbent resin such as polystyrene type porous polymer gel.

As a mobile phase, hexane, isopropyl alcohol, aqueous methanol, aqueous acetonitrile or the like may be used for the elution. Besides, counter current distribution technique that is a method for isolation and purification based on distribution between liquid phases may also be applied advantageously to the isolation and purification of the product. A solvent mixture of hexane-ethyl acetate-acetonitrile, chloroform-methanol-water or the like can be used as the distribution system.

If necessary and desired, the cell filtrate or chromatographic eluate may be treated with adsorbent resin such as highly porous resin and activated charcoal used for decoloration; the color of the filtrate or eluate is thus eliminated.

The thus obtained 6β,14α-dihydroxy-4-androstene-3,17-dione is oxidized to produce 14α-hydroxy-4-androstene-3,6,17-trione, in a conventional manner, e.g., by the method described in Japanese Patent KOKOKU (Post-Exam Publn) No. 1-32236, or its modification.

In more detail, 6β,14α-dihydroxy-4-androstene-3,17-dione is dissolved in chloroform. An oxidizing agent such as activated manganese dioxide is added to the solution to perform the oxidation. After the oxidation is completed, the reaction mixture is filtered to remove the oxidizing agent. After thoroughly washing, the solvent is removed to obtain the crude product.

The crude product is then dissolved in a small quantity of chloroform or methanol. The solution is subjected to high performance liquid chromatography using a silica gel column and an eluant (chloroform:methanol=98:2) to elute and fractionate 14α-hydroxy-4-androstene-3,6,17-trione.

The present invention is described below in more detail, by referring to the following examples but is not deemed to be limited thereto.

EXAMPLE 1

One platinum loop volume of strain NK-928521 (FERM BP-4432), which had been grown by a slant cultivation, was inoculated on 100 ml of liquid medium (3.0% malt extract, 2.0% polypeptone, 1.0% soybean meal, 0.5% $KH_2PO_4$, 0.5% $MgSO_4.7H_2O$—all concentrations expressed in terms of w/v %) charged in a 500 ml Erlenmeyer flask. Shaking culture was performed at 27° C. for 3 days to obtain a primary seed culture.

The whole volume of the seed culture was inoculated on 20 liters of liquid medium A (5% sugar, 2.0% C.S.L., 1.0% soybean meal, 0.5% $KH_2PO_4$, 0.5% $MgSO_4.7H_2O$—all concentrations expressed in terms of w/v %) charged in a 30 liter jar fermenter. Aerated agitation culture was performed at 27° C. for 3 days to obtain a secondary seed culture.

The seed culture was inoculated with a volume of 0.6 liter on 20 liters of liquid medium B (10% sugar, 2.0% C.S.L., 1.0% soybean meal, 0.5% $KH_2PO_4$, 0.5% $MgSO_4.7H_2O$, 0.75% 4-androstene-3,17-dione—all concentrations expressed in terms of w/v %) charged in a 30 liter jar fermenter. Aerated agitation culture was performed at 27° C. for 5 days.

Two liters of the thus obtained fermentation broth was diluted with 2 liters of water and 3.0% of a filtering aid was added to the dilution. The resulting mixture was filtered through a Buchner's funnel preliminarily charged with diatomaceous earth to separate into the supernatant and the cells. The filtrate thus obtained was passed through DIAION HP-20 (trademark) as adsorbent resin to adsorb 6β,14α-dihydroxy-4-androstene-3,17-dione thereto. Then elution was conducted with 60% ethanol. The eluate was concentrated under reduced pressure and the formed crystals were collected by filtration.

The crystals were dissolved in 140 ml of acetone. After turbidity of the solution was eliminated by precision filtration, 28 ml of water was supplemented to the system followed by concentration again under reduced pressure. The precipitated crystals were collected by filtration. The aforesaid recrystallization with acetone was repeated to obtain 2.4 g of 6β,14α-dihydroxy-4-androstene-3,17-dione as white powders.

EXAMPLE 2

Method of obtaining mutant:

After 10 ml of spore suspension of the strain NK-928521 (FERM BP-4432) in a concentration of 3.6×10⁵/ml was charged in a Petri dish, the suspension was exposed to UV ray for 3 minutes at 40 cm from a UV germicidal light of 15 W, while mildly stirring with a magnetic stirrer. The UV treated suspension was diluted with physiological saline to 100 to 1000-fold. Then 0.1 ml each of the dilutions was applied to a Petri dish charged with commercially available PDA (potato-dextrose-agar) medium using a glass rod, followed by cultivation at 25° C. for a week. Colonies appeared were transferred to a slant medium and cultured at 25° C. for further one week. The thus obtained mutant can be used for the production of 6β,14α-dihydroxy-4-androstene-3,17-dione, in a manner similar to Example 1.

EXAMPLE 3

Confirmation of productivity of 6β,14α-dihydroxy-4-androstene-3,17-dione by mutant:

One platinum loop volume of the mutant obtained in Example 2, which had been grown by a slant cultivation, was inoculated on 10 ml of liquid medium (3.0% malt extract, 2.0% polypeptone, 1.0% soybean meal, 0.5% $KH_2PO_4$, 0.5% $MgSO_4.7H_2O$—all concentrations expressed in terms of w/v %) charged in a test tube of 25×200 mm. Shaking culture was performed at 27° C. for 3 days to obtain a seed cultured medium. 1.5 ml of the seed cultured medium was inoculated on 50 ml of liquid medium C (5% sugar, 2.0% C.S.L., 1.0% soybean meal, 0.5% $KH_2PO_4$, 0.5% $MgSO_4.7H_2O$, 0.5% 4-androstene-3,17-dione—all concentrations expressed in terms of w/v %) charged in a 500 ml Erlenmeyer flask. Aerated spinner culture was then performed at 27° C. for 5 days.

Analysis of 6β,14α-dihydroxy-4-androstene-3,17-dione:

One g of the cultured medium described above was weighed and taken in a test tube. After extraction was performed by adding 9 ml of methanol to the medium, a part of the extract was transferred to a centrifuging tube. By centrifugation at 15000 rpm for 5 minutes, the cell debris was removed and the supernatant was quantitatively determined by HPLC under the following conditions.

Analysis column: Senshu-pak C18 6.0×150 mm
Mobile phase: acetonitrile/water=½
Flow amount: 1.0 ml/min
Column temperature: 40° C.
Detection: 240 nm
Volume of sample: 5 μl The mutant produced 1.82 mg/g of 6β,14α-dihydroxy-4-androstene-3,17-dione.

EXAMPLE 4

In 48 ml of chloroform was dissolved 1 g of 6β,14α-dihydroxy-4-androstene-3,17-dione obtained in Example 1. Then, 6 g of activated manganese dioxide was added to the solution and the reaction was carried out for several hours at room temperature. After the reaction, the manganese dioxide was removed from the reaction mixture. After thoroughly washing the reaction mixture, the solvent was evaporated off with a rotary evaporator to obtain the crude fraction.

The fraction was dissolved in a small quantity of chloroform (or methanol). The solution was applied to high performance chromatography (manufactured by Senshu Kagaku K. K.), using a silica gel column and eluant (chloroform: methanol=98:2) to elute and fractionate 14α-hydroxy-4-androstene-3,6,17-trione.

According to the present invention, 6β,14α-dihydroxy-4-androstene-3,17-dione and 14α-hydroxy-4-androstene-3,6,17-trione which have a specific biological activity and are useful as starting materials for preparing drugs can be produced more efficiently with high productivity, since undesired production of the by-products, which are hardly separable from the desired products, can be prevented as less as possible.

What is claimed is:

1. A process for the production of 6β,14α-dihydroxy-4-androstene-3,17-dione from 4-androstene-3,17-dione, said process comprising:
    culturing Myrothecium sp. FERM BP-4432, or a mutant thereof capable of hydroxylating 4-androstene-3,17-dione to produce 6β,14α-dihydroxy-4-androstene-3,17-dione, in a medium supplemented with 4-androstene-3,17-dione, and
    isolating 6β,14α-dihydroxy-4-androstene-3,17-dione from the culture medium.

2. The process according to claim 1, further comprising oxidizing said 6β,14α-dihydroxy-4-androstene-3,17-dione to produce 14α-hydroxy-4-androstene-3,6,17-trione, and
    isolating said 14α-dihydroxy-4-androstene-3,6,17-trione.

3. A biologically pure culture of Myrothecium sp. FERM BP-4432, or a mutant thereof capable of hydroxylating 4-androstene-3,17-dione to produce 6β,14α-dihydroxy-4-androstene-3,17-dione.

* * * * *